United States Patent
Svedman

[11] Patent Number: 6,138,044
[45] Date of Patent: Oct. 24, 2000

[54] METHOD AND DEVICE FOR SENSING BIOELECTRICAL SIGNALS

[76] Inventor: Pål Svedman, Chemin de Sous-Balme 9, 1255 Veyrier, Switzerland

[21] Appl. No.: 09/132,235

[22] Filed: Aug. 11, 1998

Related U.S. Application Data

[63] Continuation of application No. PCT/SE97/02093, Dec. 12, 1997.

[30] Foreign Application Priority Data

Dec. 12, 1996 [SE] Sweden ................................. 9604564

[51] Int. Cl.⁷ ...................... A61B 5/0408; A61B 5/0478; A61B 5/0492

[52] U.S. Cl. ............................................ 600/387; 600/391

[58] Field of Search ..................................... 600/382, 387, 600/391, 392; 607/149, 153

[56] References Cited

U.S. PATENT DOCUMENTS

| | | | |
|---|---|---|---|
| 3,505,993 | 4/1970 | Lewes et al. | 600/382 |
| 4,299,232 | 11/1981 | Zilianti . | |
| 4,640,290 | 2/1987 | Sherwin | 600/382 |
| 4,685,466 | 8/1987 | Rau | 600/387 |

FOREIGN PATENT DOCUMENTS

0571120 A1   11/1993   European Pat. Off. .

*Primary Examiner*—Lee Cohen
*Attorney, Agent, or Firm*—Burns, Doane, Swecker & Mathis, L.L.P.

[57] ABSTRACT

The invention relates to an electrode device (20), which for the purpose of obviating problems that have existed so far is applicable to the skin in an airtight manner for raising, by means of negative pressure and preferably heat, a portion of the epidermis and causing interstitial fluid and/or the epidermal basement membrane to contact an electrode for a measuring operation.

20 Claims, 4 Drawing Sheets

METHOD AND DEVICE FOR SENSING BIOELECTRICAL SIGNALS

CROSS-REFERENCES TO RELATED APPLICATIONS

This is a continuation of International Application No. PCT/SE97/02093, filed Dec. 12, 1997, that designates the United States of America.

BACKGROUND OF THE INVENTION

1. Field of the Invention

The present invention relates to a method and a device for sensing bioelectrical signals. More specifically, the invention concerns a method and a device for transducing the bioelectric signals that are subsequently recorded in electrocardiogram (ECG), electroencephalogram (EEG) and electromyogram (EMG) techniques.

The ECG is derived from the electrical activity of the heart and is widely used in diagnosing disturbances in cardial rhythm, signal conductance through the heart and damage due to cardiac ischemia and infarction.

2. Description of the Related Art

The tissues between the heart and the skin exhibit high electrical conductivity which the skin does not. Unsolved problems in ECG recording relate above all to the low electric conductivity in the stratum corneum of the skin. The electric characteristics of the other tissues between the heart and the skin play a comparatively small role. The electrode impedance varies not only with the integrity and moisture of the stratum corneum but also with other factors that are difficult to control, for instance the variation of skin blood flow and pressure or movement of the electrode.

A typical ECG electrode on dry skin has a contact impedance with a resistive part of about 100 k$\Omega$ and a capacitive part of about 0.01 $\mu$F. In order to establish a good contact, an electrode gel, paste or hydrogel film containing an electrolyte is applied between the skin and the metallic conductor of the electrode. This may reduce the contact impedance to R=10 k$\Omega$ and C=0.1 $\mu$F. The electrolyte may cause skin irritation, especially when the application extends over a somewhat longer time. By special procedures (multipoint electrode), the stratum corneum impedance layer of the skin can be perforated by designing the electrode as a grater which is pressed against the skin. A further variety is an electrode provided with a rubbing pad which is preliminarily rubbed against the skin. With these techniques, the contact impedance may decrease to 4 k$\Omega$, which still causes problems of detection. The above mechanical techniques are inadequate because the stratum corneum has a varying thickness in different individuals and on different body parts, and therefore the electrode impedance may vary between different electrode leads (see below).

The construction of the ECG amplifier is complicated owing to the described problems with conductivity in the skin. The input impedance of an ECG amplifier must be high in relation to the electrode impedance. If the electrode impedance is to be measured, this must be carried out by using an alternating current method, since this allows determination of both capacitive and resistive components in the tissue. Use of a direct current results in a strong polarisation of the electrodes in contact with electrolyte and skin, which generates a counter electromotive force. This results in a reduced current through the electrodes and a false high estimate of the resistance. The complexity in the measuring equipment increases when a resistive network must be utilised. In this case, an impedance conversion usually takes place by connecting a feedback amplifier before the resistance network, thereby preventing the electrode impedance from being subjected to load.

An earth connection is applied in order to limit ECG disturbances. Interference voltages are induced by capacity coupling between patient and mains voltage wires. The elimination of disturbances is rendered difficult in technical respect through differences in the electrode impedance between different electrodes. These differences may relate to the thickness of the stratum corneum, skin hydration, corneal layer traumatization and dermal perfusion blood flow. In order to minimise a capacitively transmitted disturbance in differentially connected amplifiers, use is made of an amplifier with inverse feedback which actively drives the patient to earth potential.

BRIEF SUMMARY OF THE INVENTION

The object of the present invention is to obviate the above problems with the available electrodes, and this object is achieved by means of the method and the electrode device as defined in the appended claims.

By applying suction to a limited portion of the skin surface (<6 cm diameter), the outer layer of the skin (epidermis) including the stratum corneum skin barrier is split off from the dermis. the split occurs superficially in the epidermal basement membrane, in the layer which is called lamina lucida. A blister forms which is filled with interstitial fluid. The blister roof consists of an intact expanded epidermis. The blister base constitutes an erosion. The epidermis is regenerated in about a week. The erosion heals without a scar. The suction blister technique is extensively used in dermatological research in particular. The erosion allows a dermal access route that is used clinically for the systemic delivery pharmaceutical preparations (cf. Patent Application WO 95/30410) and sampling (cf. Patent Application WO 95/08606).

The epidermal split always takes place in the basement lamina and is independent of the thickness of the corneal skin layer. The basement lamina is located superficial to the capillaries, the lymphatic vessels and the nerves in the dermis, and thus the splitting procedure does not produce pain or bloodshed. Dermal blood flow is markedly increased by release of potent vasodilating substances, and this increase in blood flow is sustained for days.

The degree of vacuum that is required to split the epidermis off as a blister is in the range of −100 mmHg to −500 mmHg (below atmospheric pressure) a pressure of −200 mmHg is most often used. The split is accomplished more rapidly when the degree of vacuum is increased. Local heating to 37–48° C. has a similar effect. In newborn infants a suction blister forms in 45 min at −200 mmHg at room temperature. In adults the process takes 10–45 min at 300 mmHg with temperature increased to 38° C.

The electrode device according to the invention allows standardized elimination of epidermis including the stratum corneum on a 1–3 mm skin spot and increased dermal blood flow. These changes eliminate of the electrode impedance in the skin. A consequence of this is that electrode leads from different parts on the body achieve similar electric conductivity.

The electrode device is also applicable for transducing electroencephalogram (EEG) and electromyography (EMG) signals, and the advantages above apply also for these techniques.

BRIEF DESCRIPTION OF THE DRAWINGS

The invention will now be described in more detail with reference to the accompanying drawings, in which.

DETAILED DESCRIPTION OF THE INVENTION

Figure 1:
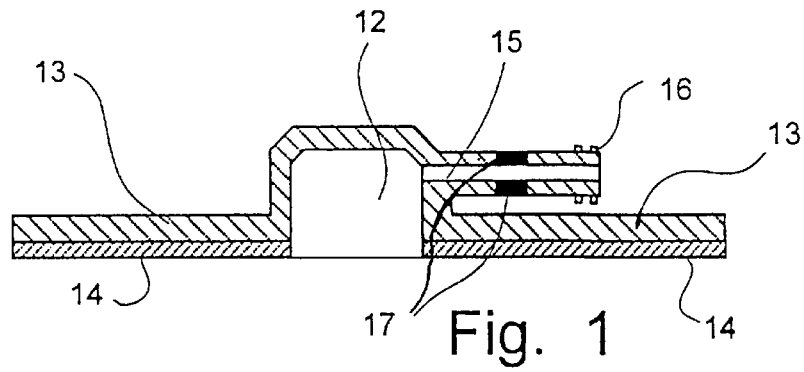
FIGS. 1–3 are exemplary embodiments of the electrode device, according to the present invention.

In its simplest form, the electrode device (see FIG. 1) is a cylindrical suction cup 12 with a flange 13 which is coated with an adhesive 14 on the side facing the skin. The suction cup is provided with a tube 15 with a luer connection 16. On the inside of the tube there is an electrode 17, which allows transduction of biosignals into electrical current; the connection to a recording device is not shown. The cylindrical part of the suction cup typically has an inner diameter of 1–3 mm and an inner height of 0.5–1.5 mm. The outer diameter of the flange suitably is 30 mm–40 mm.

The electrode device (FIG. 1) can suitably be injection moulded of e.g. Plexiglas or some suitable plastic polymer, for instance vinyl. A layer of hypoallergic adhesive (for instance acrylic adhesive) 14 may be laminated onto the entire flange 13. The acrylic adhesive layer extends all the way up to the inner edge of the cylindrical part of the suction cup. In another embodiment, the inner part (circle ring) of the flange may be laminated with acrylic adhesive and the outer part with hydrocolloidal adhesive which allows adhesiveness to moist skin in particular. The acrylic adhesive is water-repellent and prevents the interstitial fluid from coming into direct contact with the hydrocolloidal adhesive tape, which, without this adheshive skin barrier could absorb the interstitial fluid from the erosion in an uncontrollable manner. The electrode 17 may be cylindrical, suitably with an inner diameter of 0.2 mm–1.0 mm. The electrode material can be silver, brass covered with nickel or carbon. The carbon can advantageously permit the electrode to be made transparent to X-rays. The electrode may be provided with a press stud or alternatively a clamp contact, which are not shown.

Figure 2:
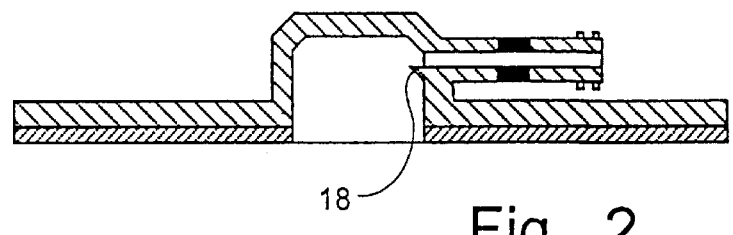

The electrode device as shown in FIG. 2 differs from the one described above by a protruding pin with or without shearing edge 18 which projects into the inner upper part of the suction cup. This pin may be moulded as an extension of the electrode cylinder.

Figure 3:
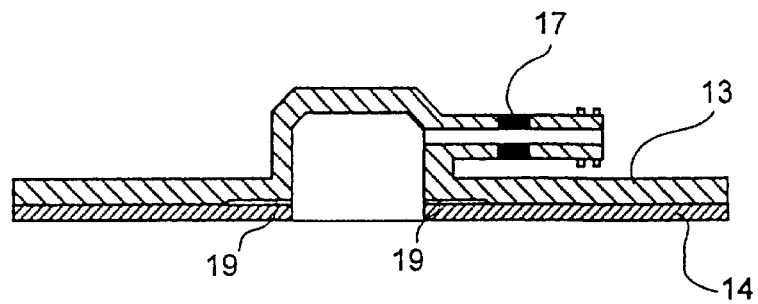

FIG. 3 shows an electrode device according to the invention with a heater 19 in the form of a circular ring, which is placed preferably on the outside of the flange, or between the flange and an adhesive layer (see above). The heater may be an integrated part of the injection moulded material or it may be adhered to the flange. The heater constitutes maximally the surface of the entire flange. It is important that heating can take place as close to the suction cup as possible, and therefore the inner extremity of the heater may maximally correspond to the inner diameter of the suction cup.

The skin is suitably heated within the temperature range of 36–43° C. The lower temperature limit for causing a burn injury is 44° C. Both passive and active (termistor regulation) temperature control is possible. In a simple passive system, the heating element consists of a mass with a predetermined temperature coefficient and resistance. A battery is selected which has suitable power generation and internal resistance to give the mass the desired temperature. In an experiment the skin of healthy subjects was heated continuously by means of a brass heater with an outer diameter of 29 mm in the range of 35–43° C. The generation of power was <0.5 W with resistance $R_b \approx 1.7 \, \Omega$.

The heater may consist of one or more layers of insulation and one or more metallic conductors. As examples of insulating material, mention can be made of PVC, polyester, silicone, rubber and micanite. The conductor material can be a resistance-causing alloy of copper, brass or aluminium with a thickness of 10–100 $\mu$m. In the heater, elements having different characteristics can be arranged side by side. One unit for rapid heating and one for maintaining a given temperature may be involved. In one embodiment, a heater may allow increased temperature in the part which is located closest to the suction cup.

In active control by means of electronics, the element or elements can suitably incorporate a sensor or thermostat for temperature monitoring to make sure that the temperature is kept constant. A PTCR (Positive Temperature Coefficient Resistor) or an electromechanical thermostat can be used for controlling the temperature. A module for temperature control may consist of two individual on-off controls with negative feedback. A maximum temperature limitation may be available on each regulator, which is adjusted via a potentiometer. The regulator can manage to hold the set temperature ±0.2° C. with NTC resistors of the ICE 539 type, $R(25° C.) = 47 \, k\Omega$.

Figure 4:
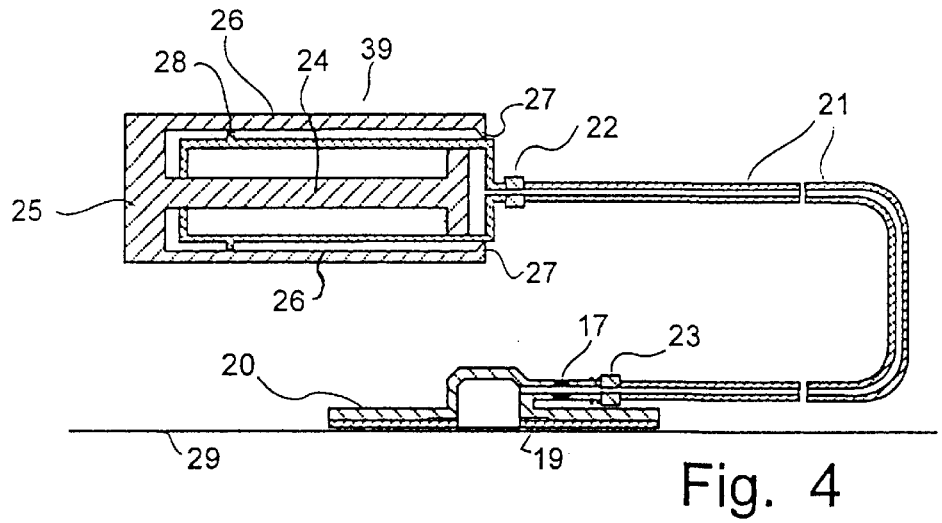
FIGS. 4–8 illustrate in chronological order the course of events when an electrode device is activated before use.

In FIG. 4, a volume expander 39 is connected to an electrode device according to the invention 20 by means of a flexible airtight tube 21. The connections 22, 23 are airtight. In the embodiment, this has been achieved by means of couplings which can be tightened by means of a screw mechanism. This screw mechanism is shown in the tube end towards the electrode device 23. The piston 24 of the volume expander passes into a handle 25 which passes into two slightly resilient arms 26, which have triangular projections 27 directed towards the outer wall of the expander. The side of the triangle facing the tube connection is at right angles with the expander. The outer wall of the cylinder is provided with a protruding, ridge 28 which is rectangular in cross-section.

The electrode device is fixed to the skin 29 in an airtight manner by means of an adhesive tape. The electrode of the device is connected to a recording device for ECG (not shown). The heater is connected to a power source (not shown), and the underlying skin surface is heated to 42–43° C.

Figure 5:
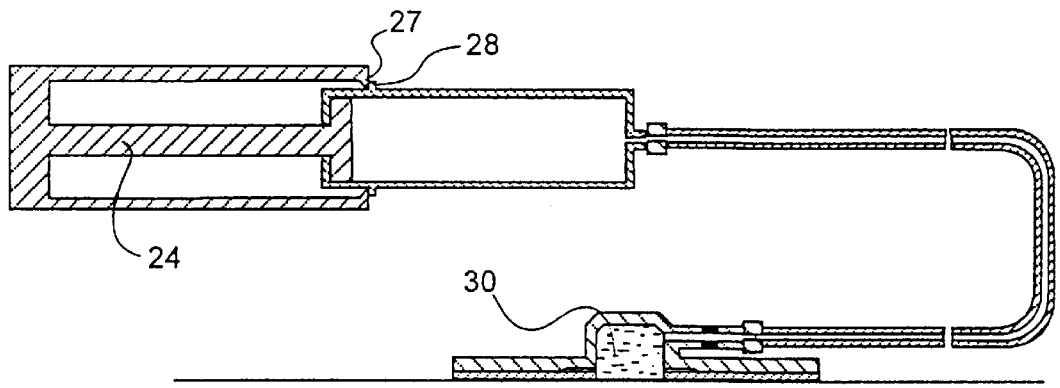

In FIG. 5, the piston 24 of the volume expander has been moved maximally backwards. The ridge 28 has been passed by the triangular projections 27 which have been able to slide unimpededly over the rectangular strip 28 with their sloping side. The negative pressure in suction cup, tube and syringe is 400 mmHg below atmospheric pressure in this maximum plunger expansion. The piston is prevented from being pulled back by the established vacuum by the right angled projection 27 not being able to slide over the ridge 28. The combination of suction and heating of the skin in and around the suction cup has made the epidermis split off the underlying dermis, and a skin blister (30) filled with interstitial fluid has formed.

Figure 6:
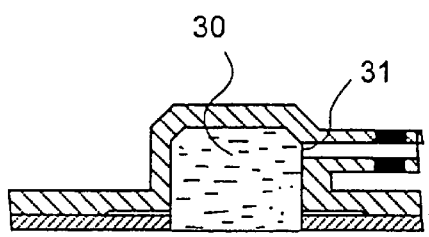
Figure 7:
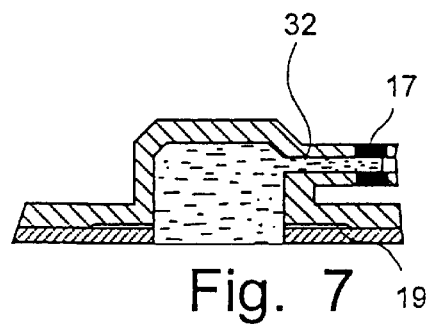
Figure 8:
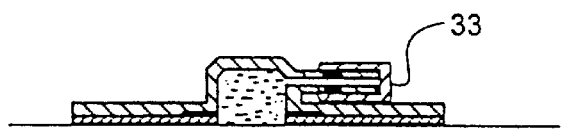

When the roof of the blister engages with the tube opening 31, the negative pressure is limited to the exposed small part of the blister roof as shown in FIG. 6. This results in a further expansion of the roof which bursts. In FIG. 7, the interstitial fluid 32 has been sucked via this opening in the skin into the tube and has come into contact with the electrode. This results typically in elimination of the skin electric impedance on the electrode device site. Relative vacuum is no longer required. The volume expander is removed, and the aparture is sealed by means of a plug 33 as shown in FIG. 8. The electrode device is now ready for use.

Experiment

Figure 9:
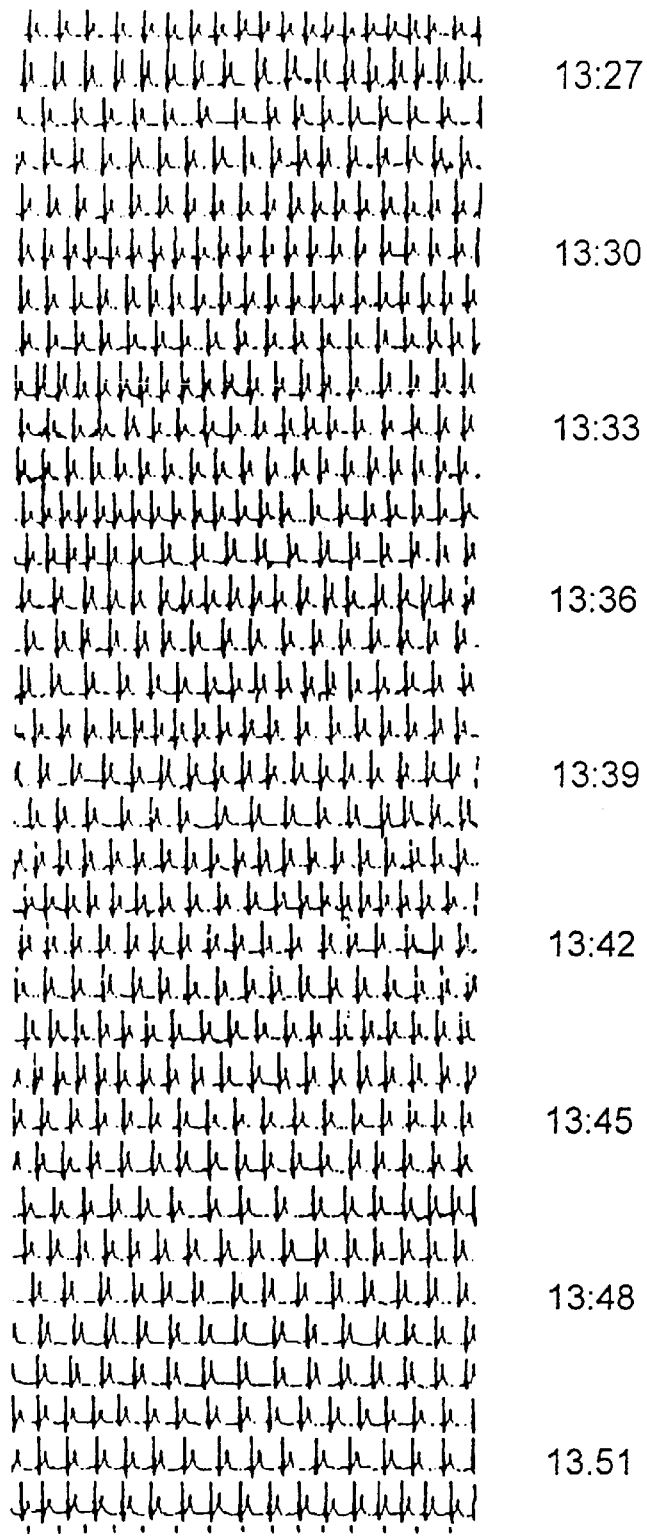
FIGS. 9 and 10 are ECG curves recorded by means of the electrode device according to the present invention and by a conventional electrode, respectively.
Figure 10:
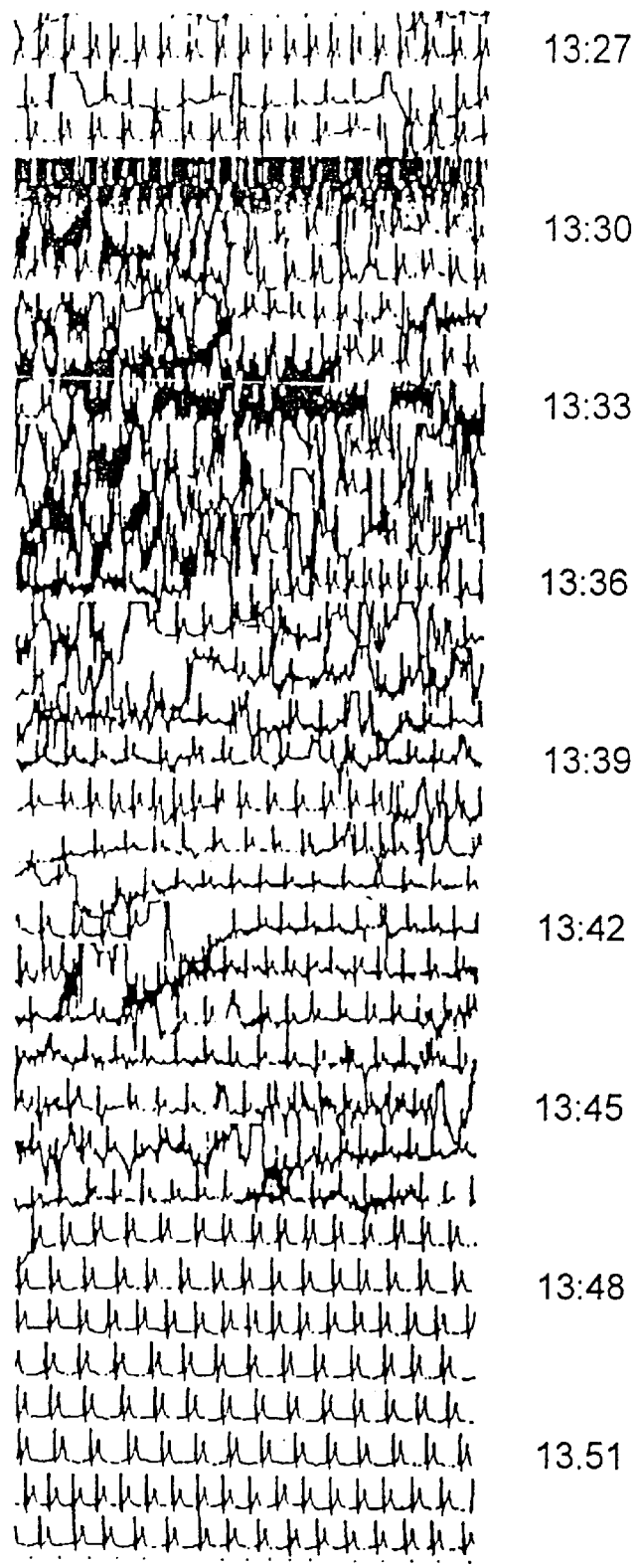

Continuous ECG recordings in a healthy volunteer using electrode devices according to the invention and conventional electrodes as control. FIG. 9 shows a recording using electrode devices according to the invention, and FIG. 10 a recording using conventional technique during the same period. The electrode devices according to the invention and conventional electrodes (Ag/AgCl in adhesive gel) were adhered to the skin side by side. The respective leads were separately supplied to two identical portable ECG devices used for long-term recording. Recordings were made during 12 h with the volunteer engaged in normal activities. A comparison of the ECG recordings was done by computerised processing, using exclusion criteria defined according to clinical practice. When using the Ag/AgCl electrodes is was not possible to read the ECG for 8487 s, and with electrode devices according to the invention for 20 s.

What is claimed is:

1. A method for deflecting electric currents for measuring ECG, EEG, or EMG on a patient, comprising steps of:
   generating negative pressure to separate epidermis from dermis of the patient to produce a blister;
   puncturing the blister by creating an opening in the epidermis; and
   positioning an electrode used in the measurement to be in contact with the patient's epidermal basement membrane and/or with a water-based medium communicating with the basement membrane through the opening in the epidermis for elimination of electrode impedance.

2. A method as claimed in claim 1, wherein the water-based medium is interstitial fluid.

3. A method as claimed in claim 1, wherein the water-based medium is an aqueous medium which contains a water-based solution or gel with electrically conducting ions.

4. A device for deflecting electric currents for measuring ECG, EEG, or EMG on a patient, comprising:
   a suction cup with adhesive flange which has a cavity which is adapted to be open to epidermis of the patient;
   means for generating a negative pressure in the suction cup, such that the epidermis is made to separate from dermis of the patient, for producing a blister;
   means for penetrating or puncturing the blister; and
   wherein an electrode within the suction cup is movable into contact with the epidermal basement membrane or arranged at a distance from a surface thereof and surrounded by an electrically conducting, water-based medium.

5. An electrode device as claimed in claim 4, wherein the means for penetrating the blister is a cutting pin.

6. An electrode device as claimed in claim 5, wherein the suction cup is combined with a temperature-controllable heater formed as a plate, for abutting the epidermis.

7. An electrode device as claimed in claim 5, wherein said adhesive flange of the suction cup is a circumferential flange which on its side adapted to be facing the epidermis has a coating adhering to the epidermis and producing airtightness.

8. An electrode device as claimed in claim 5, wherein the suction cup is hemispherical with a tube located in an upper part of the hemisphere.

9. An electrode device as claimed in claim 5, wherein the electrode is arranged inside of a tube.

10. An electrode device as claimed in claim 4, wherein the means for puncturing the blister is the generated negative pressure.

11. An electrode device as claimed in claim 10, wherein the suction cup is combined with a temperature-controllable heater formed as a plate, for abutting the epidermis.

12. An electrode device as claimed in claim 10, wherein said adhesive flange of the suction cup is a circumferential flange which on its side adapted to be facing the epidermis has a coating adhering to the epidermis and producing airtightness.

13. An electrode device as claimed in claim 10, wherein the suction cup is hemispherical with a tube located in an upper part of the hemisphere.

14. An electrode device as claimed in claim 10, wherein the electrode is arranged inside of a tube.

15. An electrode device as claimed in claim 4, wherein the suction cup is combined with a temperature-controllable heater formed as a plate, for abutting the epidermis.

16. An electrode device as claimed in claim 15, wherein said adhesive flange of the suction cup is a circumferential flange which on its side adapted to be facing the epidermis has a coating adhering to the epidermis and producing airtightness.

17. An electrode device as claimed in claim 15, wherein the suction cup is hemispherical with a tube located in an upper part of the hemisphere.

18. An electrode device as claimed in claim 4, wherein said adhesive flange of the suction cup is a circumferential flange which on its side adapted to be facing the epidermis has a coating adhering to the epidermis and producing airtightness.

19. An electrode device as claimed in claim 4, wherein the suction cup is hemispherical with a tube located in an upper part of the hemisphere.

20. An electrode device as claimed in claim 4, wherein the electrode is arranged inside of a tube.

* * * * *